(12) United States Patent
Milbocker

(10) Patent No.: US 9,079,034 B2
(45) Date of Patent: Jul. 14, 2015

(54) METHOD FOR STABILIZATION OF CARDIAC TISSUE CONTRACTIONS USING LIMIT CYCLES

(71) Applicant: Technology Innovation, LLC, Pittsford, NY (US)

(72) Inventor: Michael T. Milbocker, Holliston, MA (US)

(\*) Notice: Subject to any disclaimer, the term of this patent is extended or adjusted under 35 U.S.C. 154(b) by 113 days.

(21) Appl. No.: 13/875,720

(22) Filed: May 2, 2013

(65) Prior Publication Data

US 2013/0296959 A1 Nov. 7, 2013

Related U.S. Application Data

(60) Provisional application No. 61/641,455, filed on May 2, 2012, provisional application No. 61/789,553, filed on Mar. 15, 2013.

(51) Int. Cl.
*A61N 1/362* (2006.01)
*A61N 1/365* (2006.01)
*A61N 1/39* (2006.01)

(52) U.S. Cl.
CPC .......... *A61N 1/36592* (2013.01); *A61N 1/3621* (2013.01); *A61N 1/3987* (2013.01)

(58) Field of Classification Search
CPC A61N 1/36592; A61N 1/3621; A61N 1/3987
See application file for complete search history.

(56) References Cited

U.S. PATENT DOCUMENTS

| | | | |
|---|---|---|---|
| 4,603,705 | A | 8/1986 | Speicher |
| 4,848,352 | A | 7/1989 | Pohndorf |
| 5,447,520 | A | 9/1995 | Spano |
| 5,482,037 | A | 1/1996 | Borghi |
| 5,522,863 | A | 6/1996 | Spano |
| 5,620,468 | A | 4/1997 | Mongeon |
| 5,797,965 | A | 8/1998 | Spano |
| 5,797,967 | A | 8/1998 | KenKnight |
| 5,840,079 | A | 11/1998 | Warman |
| 6,081,746 | A | 6/2000 | Pendekanti |
| 6,085,116 | A | 7/2000 | Pendekanti |
| 6,157,862 | A | 12/2000 | Brownlee |
| 6,246,906 | B1 | 6/2001 | Hsu |
| 6,292,691 | B1 | 9/2001 | Pendekanti |
| 6,327,500 | B1 | 12/2001 | Cooper |
| 6,526,317 | B2 | 2/2003 | Hsu |
| 6,539,260 | B1 | 3/2003 | Schloss |
| 6,556,862 | B2 | 4/2003 | Hsu |
| 6,587,720 | B2 | 7/2003 | Hsu |

*Primary Examiner* — Michael Kahelin

(74) *Attorney, Agent, or Firm* — Ideation Law, PLLC; Joseph P. Kincart

(57) ABSTRACT

Electrical stimulation to cardiac tissue stabilizes atrial and ventricular arrhythmia when timed to stabilize a limit cycle structure in a Poincare map. Disclosed are methods and apparatus, operational internally or externally, for removing the reentrant effects of heterogeneity present in a diseased heart and returning the heart to an improved metabolic status allowing removal of support. The methods and apparatus disclosed are also useful in the chronic surveillance and maintenance of regularized contractility in an aged or diseased heart.

17 Claims, 1 Drawing Sheet

METHOD FOR STABILIZATION OF CARDIAC TISSUE CONTRACTIONS USING LIMIT CYCLES

CROSS-REFERENCE TO RELATED APPLICATIONS

This application is a non-provisional of U.S. Patent Application Ser. Nos. 61/641,455 (filed May 2, 2012) and 61/789,553 (filed Mar. 15, 2013) the entirety of which are incorporated herein by reference.

BACKGROUND OF THE INVENTION

Electrical activity in the human heart originates in the right atrium (RA) in the sinoatrial (SA) node as a wave. This wave of activation spreads quickly across the atria to the atrioventricular (AV) node. The AV node serves to delay the wave of activation relative to activation of the ventricle. The delay results in contraction of the atrium before the ventricles contract. After the activation is delayed by the AV node, the activation wave enters and excites the bundle of His. Excitation of the bundle of His results in propagation through the Purkinje fibers of a plane wave structure across the ventricles through the ventricular conduction system. Excitation spreading through the conduction system activates each ventricular cell at a precise time relative to activation from the bundle of His (known as the "Phase") to produce a phased ventricular contraction. For regular cardiac contraction, both atrial and ventricular, it is important that each contractile cell possess only one phase value during a contraction cycle. When these phases multiply within a contractile cycle, the result is arrhythmia.

In the case of ventricular arrhythmias, for various reasons both conductive and structural, the function of the AV node can be compromised (AV block). AV block inhibits or prevents utilization of the normal conduction systems of the ventricles. Ventricular pacing has been used for treating heart rhythm disorders when a normal conduction system (free of heterogeneities) cannot be utilized due to AV block. However, ventricular pacing does not reproduce the precise wave front structure characteristic of the AV node, which is responsible for the optimal spatial and temporal electrical actuation of the ventricular cells that is required for optimal hemodynamic function of the heart. Pacing induced inefficiency has been associated with an increased occurrence of congestive heart failure, desynchronized contractions, negative inotropic effects, histological and ultra-structural changes in ventricular tissue.

Alternative pacing sites, for example, the right ventricle (RV) generally, RV outflow tract (RVOT) and various septum sites have been investigated relative to improving cardiac hemodynamics during pacing. Direct His bundle pacing has also been used in an attempt to achieve synchronized ventricular contraction in patients with an intact ventricular conduction system. However there can be limitations associated with His bundle pacing in humans. For example, studies have reported difficulty in pacing the relatively small area of the His bundle and difficulty inserting a pacing lead into the membranous septum. Further, higher pacing and lower sensing thresholds can be required for His pacing than for RV pacing due to the high fibrous content of the His region. Also, because His bundle pacing site is located close to the aorta, there are potentially devastating consequences due to damage of the aorta.

Single source pacing modalities universally are incapable of reproducing the synchrony achieved by a healthy AV node. Accordingly, resynchronization therapy has been advanced by utilizing multiple ventricular pacing sites, such as biventricular pacing. While the multiple-lead approach provides greater versatility in achieving the required physiological degree of synchrony, control algorithms have not been devised to take advantage of this increased control dimensionality.

One form of regularization is cardioversion. Cardioversion attempts to reset all electric activity in the atria and requires the use of large (5V/cm) electric field gradients. These high energies cause pain and trauma for the patient, damage the myocardium, and reduce battery life in implanted devices. Another strategy, anti-tachycardia pacing (ATP), seeks to avoid the development of permanent atrial fibrillation (AF) by suppressing paroxysmal AF. ATP consists of a train of 8 to 10 low-energy stimuli delivered as a pacing ramp or burst at 50 Hz via a single pacing electrode. ATP is effective in treating spontaneous atrial tachyarrhythmia, especially slower tachycardia, but it is not very effective for converting AF.

Predicting propagation patterns of the in situ heart is an arduous task, especially when the anatomic and functional complexity of a diseased heart is considered. Technical challenges are involved in recording propagation patterns in an intact organ at temporal and spatial resolution sufficient to reveal the interactions of rotating waves and paced wave fronts.

The pacing aspect is especially complicated. After an electric field pulse is applied to the heart, "virtual electrodes" may arise at interfaces separating regions with different conductivities. These sites may be macroscopic, such as blood vessels or ischemic regions, or smaller-scale discontinuities, including areas of fibrosis or abrupt changes in fiber direction. Virtual electrodes arise when the activation wave energy is re-radiated in a manner analogous to optical reflection and diffraction from tissue conductive and structure discontinuities. In the application of pacing pulses, a virtual electrode is a secondary source of an activation wave. The character of this secondary activation wave is highly dependent on the extent of the conductivity discontinuity and the strength of the applied electric field.

Consider now how an activation site develops on application of an electric field in cardiac tissue containing a generic conductivity discontinuity between myocardium and an inexcitable inhomogeneity. When an electric field is applied, current flows out of the electrode and through the extracellular medium and enters the tissue at the tissue edge and subsequently exits at the boundary of the inexcitable region. Similarly, on the other side of the inexcitable region, current re-enters the tissue at the boundary. In quiescent tissue, this current produces depolarization (hyperpolarization), and in the conducting region along all interface boundaries where the excitable tissue is closer to the electrode. If the depolarized region reaches the threshold for excitation, it can initiate propagating waves, thereby serving as an activation site, also known as a secondary source, or virtual electrode.

Virtual electrode formation has been demonstrated to terminate fast atrial tachycardias and AF. In this method, electrodes located at a small distance from the heart deliver a train of low-voltage shocks at a rapid rate. During the low-energy shocks, small intrinsic conductivity discontinuities behave as internal "virtual" electrodes. The virtual electrodes serve as activation sites if the field strength depolarizes the tissue beyond the excitation threshold. At low field strengths, only a single virtual pacing site may be created, whereas at slightly higher field strengths, many more activation sites arise, and the time required to excite a given myocardial region decreases. The greater the number of virtual electrodes that are formed as a consequence of external excitation, the easier it is to regularize the temporal aspect of cardiac tissue contractility.

Virtual electrode formation as a therapy is ironically analogous to one of the primary causes of cardiac arrhythmia. Many arrhythmias are caused or maintained by what are clinically called reentry mechanisms. Reentry is a condition in which cardiac tissue continually excites itself, creating reentrant, e.g. circular or tornado-like patterns of excitation. Reentry circuits are described morphologically, for example a macro-reentrant circuit is characterized by rotation around a functional or anatomic line of block. Major anatomical structures are usually involved in defining one or several simultaneous reentry circuits, including the region between superior and inferior venae cavae in the right atrium, and the pulmonary vein region in the left atrium. If the cycle length (CL) of the reentry remains relatively long, one-to-one conduction can remain throughout the entire atrium or ventricle. However, if the CLs of reentry circuits are sufficiently short, waves of excitation produced by the reentrant circuit break up in the surrounding tissue and fibrillation can ensue.

There are distinctions between a regular high frequency rhythm state (tachycardia) and fibrillation. The high frequency state is defined as the presence of a single, constant, and stable reentrant circuit. The fibrillation state is characterized by random activation in which multiple reentrant wavelets of the primary activation wave continuously circulate in directions determined by local excitability, refractoriness, and anatomical structure. The consequence is a multiplicity of spatially localized frequencies created by wave front annihilations. Fibrillation can sometimes be converted to tachycardia, and vice versa, spontaneously or as a result of an intervention, such as drug administration, DC cardioversion/defibrillation, or pacing.

The discussion above is merely provided for general background information and is not intended to be used as an aid in determining the scope of the claimed subject matter.

BRIEF DESCRIPTION OF THE INVENTION

This disclosure relates in general to monitoring, analyzing and modifying the electrical behavior of cardiac tissue, and in particular relates to devices that function to regularize and diminish the frequency of the electrical behavior of living cardiac tissue. More particularly, this disclosure relates to regularization of the frequency of contraction in atrial and ventricular tissue of the human heart.

Electrical stimulation to cardiac tissue stabilizes atrial and ventricular arrhythmia when timed to stabilize a limit cycle structure in a Poincare map. Disclosed are methods and apparatus, operational internally or externally, for removing the reentrant effects of heterogeneity present in a diseased heart and returning the heart to an improved metabolic status allowing removal of support. The methods and apparatus disclosed are also useful in the chronic surveillance and maintenance of regularized contractility in an aged or diseased heart.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1A:
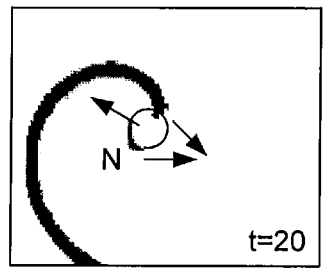
FIG. 1A, FIG. 1B, FIG. 1C and FIG. 1D depict the unpinning of a reentrant wave.

The realization that many activities of an apparently random nature are actually examples of a deterministic phenomenon known as chaos offers a new approach to analysis and modification of the type of complexity exhibited by cardiac tissue.

The electrical impulses that normally cause sinus rhythm are thought to progress repeatedly around irregular conduction pathways within the heart. These conditions, if uncontrolled, can become life threatening if the aberrant electrical impulses enter the atrioventricular node (AV node) in a sporadic and/or at an accelerated rate and can cause an irregular ventricular rate that degenerates into an immediate life threatening ventricular arrhythmia.

To quantitatively characterize the response of a global arrhythmia to a single pulse stimulus, one can calculate Poincare maps which can be used to anticipate the system response when a therapeutic pulse is applied. For example, one generates a Poincare space plot comprised of global periodicity at time T on one axis and global periodicity at T+1 on the other axis. When this plot is constructed over several periods, one sees high and low density regions, the high density regions typically depict a ring-like structure, and these ring-like structures in the Poincare space plot are called limit cycles. They are important because when the system enters a limit cycle it is possible to predict with a high degree of confidence the subsequent beat period, and indeed a whole series of beat periods until the system leaves the limit cycle. It is therefore, stabilizing to apply therapeutic pulses that tend to keep the system on a desired limit cycle. In so doing, the perturbative interference patterns that result between reentrant circuits are disrupted in favor of maintaining the limit cycle period.

Limit cycles are not the same thing as heart rate or beat frequency. Limit cycles describe the range of periods which occur while on the limit cycle. Each point in a limit cycle represents a single beat frequency. It is therefore, possible to pick a limit cycle which is small in area, with fewer points, and consequently low in beat frequency variability. The distance between points is linearly related to a difference in beat frequency. On the other hand, variability can be tolerated as long as the range of beat frequencies is maintained below a certain pathological limit. Thus regularization in itself, is not necessarily the ideal outcome, but rather overall reduction in beat frequency, thus enhancing the amount of blood moved after each contraction.

Although limit cycles are not beat rates, they are temporally cyclic and possess a phase and period. Consequently, a large area limit cycle can be reduced in area by making use of the Poincare limit cycle structure. For example, two nearby limit cycles, one having a clinically desirable character the other comprising the current cardiac state, can be used to shift the cardiac dynamics from one limit cycle to a particular limit cycle.

In addition, by applying a properly timed pulse, the system can be caused to jump from one point on a limit cycle to another point on the same limit cycle, but several beats ahead of where it would have gone in the next beat cycle. We call this phenomenon limit cycle collapse, and in ideal applications of the therapy a generally circular limit cycle is collapsed to a near linear structure. This is an important step in achieving regular heart rate. Thus an additional map can be constructed comprising the phase of the limit cycle immediately before the pulse to the induced limit cycle phase after the pulse. The limit cycle phase change is computed from the difference between the perturbed and the unperturbed point positions on the limit cycle period and the change in phase is assumed to happen instantaneously with the pulse Another beneficial aspect of the limit cycle approach is that the pulse width need not match the cardiac periodicity. In particular, fibrillation is characterized by extremely short periods, which in reality may just be the result of interference between a number of independent longer periods at localized sites on the cardiac tissue. Therefore, matching the fibrillation period may actually not be matching to any one of the independent local periods. In order to be successful in stabilizing a cardiac arrhythmia, it is important to stimulate a period that reflects an actual activation wave front cycle, otherwise such action on a combined signal may only serve to reinforce the chaotic behavior of the system.

In an aspect of the present disclosure, a method for destabilization and termination of atrial/ventricular tachyarrhythmia includes detecting a tachyarrhythmia initiated from sensing of electrical activity, estimating a minimum or dominant limit cycle, this limit cycle likely reflects the various rotor cycles that become manifest over a much longer period than the fibrillation period. Thus by picking a dominant limit cycle one is selecting a subset of the reentrant circuits to enhance. Reduction of the dimensionality of the limit cycle, reflected in its area, naturally tends to reinforce certain cycles and depress others, while avoiding reinforcing the interference behavior produced by the interaction of multiple reentrant cycles. However, the spatial and temporal parameters for introduction of a therapeutic signal are entirely detached from the fibrillation period, which can be quite short, and such signals wherever or whenever introduced are destabilizing by virtual of their non-physiological characteristics.

Therapies may include administration of stimulative pulses to both the atria and ventricles, sensing ventricular electrical activity to detect a ventricular R-wave, determining ventricular vulnerable period using R-wave detection to prevent or inhibit induction of ventricular fibrillation by atrial shock, determining the atrial excitation threshold by applying electrical shock through different implanted atrial defibrillation leads and subsequently sensing for atrial activation, determining pain threshold by a feedback circuit that uses information provided by the patient during both the implantation and calibration procedure, and during the execution of the device learning algorithms, determining the ventricular far-field excitation threshold by applying electrical shock through different implanted atrial defibrillation leads and subsequently sensing for ventricular activation, delivering far-field stimuli to the atria by sequentially delivering several pulses at energies above the atrial excitation threshold, wherein the electrical current at each of said implanted leads is delivered at a rate of approximately about 100% to about 1000% of the minimal cardiac beat frequency, and wherein if arrhythmia termination is not achieved by far-field shocks, the method further comprising delivering near (or far-field) atrial pacing with cycle lengths from about 100% to about 1000% of sensed atrial cycle lengths, determining whether arrhythmia termination is achieved, and wherein if arrhythmia termination is not achieved as determined by the aforementioned steps, then a sequence of therapies are repeated one or more times with a higher amplitude of electrical current and/or different lead configuration and stimulus parameters until defibrillation of the target tissue is achieved.

It is an observation original to the realization of the present disclosure in that cardiac chaotic systems display a unique characteristic. In untreated arrhythmia the state point being transient monotonically approaches an unstable fixed point from which it is repelled, consequently a perturbation forcing the system state point onto a stable manifold (limit cycle) is clinically beneficial.

Here we introduce the notion of proportional perturbation feedback. The concept is important since the difference between convergence to a stable limit cycle and pure chaotic motion is often dictated by this consideration. In many cases a system state point will naturally move toward the unstable fixed point rather than away from it, in sharp contrast to prior art methods wherein the stable manifold would instead be moved toward the current system state point. Pursuant to such prior art methods, as well as in the present disclosure, a limit cycle representation of the dynamics in the neighborhood of the desired unstable fixed point is utilized. According to prior art theory however, a system-wide parameter must be varied to move the stable manifold toward the system state point, whereas movement of the system state point toward the stable manifold by proportional perturbation feedback is effected pursuant to the present disclosure without parameter change. Such proportional perturbation feedback methodology is particularly useful where the cardiac tissue preparation possesses no system-wide parameter that can be changed with sufficient rapidity to implement corrective control.

There are various strategies for decoupling cause from effect which are primarily centered on identifying key parameters in the system. Practical approaches break into two types: 1) strategies which do not attempt to take the system out of the chaotic regime but use the chaos to control the system and 2) strategies which remove the effect of an irreversible condition such as a cardiac inhomogeneity. It is believed that both these approaches are flawed, the former requiring constant administration of a perturbative signal to maintain contractile regularity, whereas the latter is imprecise and only occasionally coincides with the receptive period of cardiac tissue. In the present disclosure, these approaches are combined by bringing the precision of the chaos approach to the approach of removing reentrant circuits originating from cardiac inhomogeities. The cardiac tissue is restored to a normal state, as if there were no cardiac inhomogeneities, wherein normal rhythm is restored sufficiently to afford a high performing metabolic state which after a lapse of time renders the cardiac tissue less sensitive to cardiac inhomogeneity and thus provides a therapy which is curative rather than supportive.

A beneficial feature of chaotic systems is their extreme sensitivity to perturbations, making it possible to achieve significant changes in system dynamics with relatively low amplitude perturbations. For example, in the case of cardioversion a signal is delivered of sufficient amplitude to reset the states of all the cardiac tissue, whereas in the case of ATP, a pulse is delivered, albeit randomly, during the receptive period of cardiac tissue sufficient to momentarily restore a more normal rhythm. Both of these approaches are best characterized as acute perturbations, which are effective due to repeated applications, each of which have a certain probability to stimulate the heart to beat at a more regular rate.

One aspect of chaotic systems which make them particularly susceptible to clinical intervention is the observation that chaotic motion includes an infinite number of unstable periodic motions. A chaotic system never remains long in any one of the universe of unstable motions but continually switches from one periodic motion to another, thereby giving the appearance of randomness. Consequently, chaotic cardiac tissue will spend some fraction of time in a clinically beneficial period, whereby external stimuli can be applied to reinforce the frequency and duration at which the cardiac tissue visits this contractile periodicity.

Control of chaos is based on the existence of chaotic attractors which create a multiplicity of unstable periodic orbits. In the continuous system state representation there are an infinite number of these unstable periodic orbits. However, a Poincare map can be constructed which is orthogonal to the flow in the continuous system state representation, such that a continuous path in the system state representation maps one point in the Poincare space discretely into another point in the Poincare map. The Poincare map is a lower dimensional representation of the system state representation. Accordingly, the multiplicity of stable and unstable orbits in the system state are condensed to stable and unstable manifolds in the Poincare state, wherein all the stable and unstable orbits of the system state representation are represented as stable and unstable lines (manifolds), usually just one of each, in the Poincare map.

The intersection of a stable manifold and an unstable manifold forms what is called in mathematics a saddle type dynamic structure, wherein the system state approached an unstable fixed point in the Poincare map along the stable manifold and moves away from the unstable fixed point along the unstable manifold, hence the fixed point is inherently stable. Chaos control essentially comprises perturbing the system such that it remains on the stable manifold, always approaching the unstable fixed point. The result is to render an otherwise chaotic behavior more stable and predictable, which is often an advantage. The perturbation must be tiny, to avoid significant modification of the system's natural dynamics.

Several techniques have been devised for chaos control, but most are developments of two basic approaches: the OGY (Ott, Grebogi and Yorke) method which involves discrete system perturbations, and Pyragas which involves continuous control. Both methods require a previous determination of the unstable periodic orbits of the chaotic system before the controlling algorithm can be designed. In the present disclosure, a novel implementation of an OGY-type technique is employed.

There is therefore a need for a method and apparatus for manipulating chaotic behavior based on assessment of chaotic regimes and by intervention at irregular times determined from real time calculations involving data obtained by monitoring a selected observable system behavior such that reentrant circuits are consistently annihilated.

This approach would clinically enhance the success rate of the ATP methodology. Existing mechanism-based strategies for increasing ATP success rates are in high demand, since this important task remains largely empirical. ATP success has been found to correlate with the electrical perturbation of a reentrant circuit at vulnerable moments called the vulnerability window (VW). The two approaches to enhancing ATP success are a VW-based methodology and a pacing-induced wave front drift methodology. Unfortunately, these two approaches are contradictory in that they are based on adjusting the pacing frequency in opposite directions.

In the VW-based methodology, a retrograde wave front is generated when a stimulus is placed within the partially recovered tail of a rotating wave. In this scenario, a multiplicity of pulses are needed to ensure random coincidence with the VW. For example, if Ps is the period of a spiral wave rotation and Pp is the period of the paced waves, then Ps−Pp should not exceed the width of the VW. If this condition is met, then arbitrary placement of the first pulse will ensure that the time of subsequent pulses will be systematically shifted with respect to the tail of the rotating wave, such that, with enough pulses, one pulse will eventually be placed within the VW. If the condition is not fulfilled then the probability of successfully placing a pulse within the VW is greatly reduced, and it is possible that the number of pulse trains required for successful ATP would increase to an impractical number. Therefore, pacing frequency should not significantly exceed the rotational rate of reentry. On the other hand, the velocity of pacing-induced drift can be accelerated by increasing pacing frequency. Consequently, the rotating wave is pushed away faster with increasing Ps−Pp (the sole limitation being tissue capture). Therefore, the drift-induced pacing mechanism leads to a strategy opposite to that derived from the VW methodology. This seemingly contradictory set of requirements is resolved in the present disclosure.

There is a need for a cardiac contraction regularization methodology that is not solely based on annihilating reentrant circuits by chance, especially when these methodologies are most successful when only one reentrant circuit occurs. In cases of multiple reentrant circuits, the result is chaos, which negates the effectiveness of the coherent approaches based on destructive wave front superposition. The concept of a vulnerability window is ill-defined in this instance, and finding a suitable maximal annihilation paradigm requires a higher concept than physical actuation wave rotation. It requires introduction of the concept of limit cycle structure in a chaotic system, which simply stated is the net effect of multiple reentrant loops on the dynamics of the system. Identification of the limit cycle structure and not individual reentrant loops is the object of the present disclosure and are among the key parameters with which to achieve contractile regularization.

Tachycardia is defined as any state of cardiac tissue contractility, ventricular or atrial) in which the activation rate exceeds nominal values of about 100 cycles per minute. Fibrillation is defined as any state of cardiac tissue contractility, ventricular or atrial, in which the beat frequency is high (>200 per minute) or the frequency is variable, often in a chaotic way. Limit cycle is defined as a parameter space in which the time sequence or beat period or analogous parameters are temporally represented such that a closed circuit is formed in the representation space. System state space is a two or more dimensional representation where the position is plotted on one to three axes and the activation state is plotted on another axis and time is plotted on yet another axis. The system state space at one moment in time is essentially a one-to-one map of the actual dynamics occurring in the cardiac tissue. Poincare space is a representation of lower dimension than the system state space. We can view the evolution of system states as a flow along the time axis. The Poincare space is a slice of the system state space that is orthogonal to the time axis. Formally, an n-dimensional deterministic dynamical system is traversed by a surface of section S with dimension (n–1) that is traverse to the flow, e.g., all trajectories starting from S flow through it and are not parallel to it. Then a Poincare map is a mapping from S to itself obtained by following trajectories from one intersection of the surface S to the next. Poincare maps are useful when studying swirling flows near periodic solutions in dynamical systems. Mother rotor is a primary actuation wave associated with an heterogeneity with a morphology similar to a spiral or radially emanating wave with center located at the heterogeneity. Rotors originate when a normal planar actuation wave is diverted by an heterogeneity in such a way that a portion of the diverted wave is rotated 180 degrees and interacts with the next incoming planar wave. This action leads to arrhythmia.

The methods and devices of embodiments of the present disclosure can utilize a low-voltage phased unpinning far-field therapy to destabilize or terminate the core of a mother rotor anchored to a myocardial heterogeneity such as the intercaval region or fibrotic areas. More importantly, the present disclosure terminates chaotic dynamics arising from the interference of multiple rotors, which is generally associated with eventual decay into a lethal fibrillation state. An approximate 100-fold reduction in stimulus energy can be obtained with this unpinning method compared with conventional high-energy defibrillation, and an approximate 5-fold reduction in stimulus energy used in conventional ATP therapy. These methods and devices achieve cardioversion in the case of the atria and defibrillation in the case of the ventricles without exceeding the pain threshold of a patient. The aforementioned also significantly reduce the energy storage requirements of implantable devices.

Figure 1B:
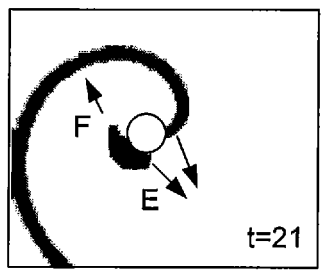
Figure 1C:
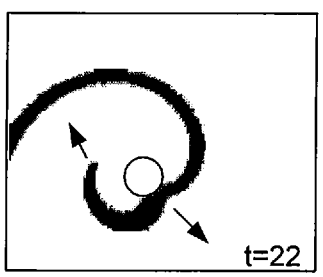
Figure 1D:
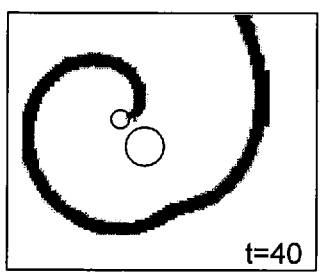

In considering a single reentrant circuit, the success of the unpinning mechanism depends on the position of the spiral activation wave at the time of administration of the therapeutic pulse, taking into consideration the delays involved between the source electrode and the reentrant center. The position of the reentrant center is typically referred to as the phase zero position, conventionally chosen as the source of far-field pulse wave nucleation. As illustrated in the successful unpinning of FIG. 1A, FIG. 1B, FIG. 1C and FIG. 1D, there is a finite unpinning window of phases in which unpinning is possible in the way depicted. In FIG. 1A, an externally applied far-field pulse nucleates (N) a wave. In FIG. 1B, a new wave (F) rotates counter to the reentrant circuit. In FIG. 1C, as the far-field induce wave evolves it impinges on the reentrant wave, causing decoupling (see FIG. 1D) of the reentrant wave from the center of inhomogeneity.

The above reentry rectifying strategy is applicable only to single focal centers. When one considers several such centers, the evolving reentrant spirals impinge on adjacent spirals resulting in dynamics that propagate beyond any one local spiral geometry. One can consider the evolution of cardiac tissue contractility as a whole as a system of coupled oscillators, each with different characteristic frequencies connected through specific temporal delays.

To address the limitations inherent in ATP therapy, we disclose a new method of destabilizing and subsequently terminating multiple coupled anatomical reentrant tachyarrhythmic regions in which a low-voltage shock is applied to unpin limit cycles resulting from the superposition of multiple oscillatory states. This method uses the effect of virtual electrode polarization (VEP), which is representative of hyperpolarization and depolarization on opposite sides of a functional or anatomical heterogeneity in response to an applied external electrical field. However, we are not concerned with a single anatomical heterogeneity, but the combined effect of multiple heterogeneities as manifest in the limit cycle structure. Accordingly, we have generalized the VEP concept to this specific multi-oscillator limit cycle structure.

Generally, the approach entails coordinating multiple areas of depolarization which give rise to secondary sources of excitation with pulse application such that secondary sources arising from the pulse therapy address the global tissue heterogeneity that also serves as the core of reentry of the global limit cycles. Because all possible reentry cores are simultaneously excited with a single low-voltage pulse, the Poincare or time of transmission become important. Consequently, this method most beneficially relies upon multiple sources, similar to resynchronization pacing, to provide extinction wave fronts to a multiplicity of reentrant centers with a multiplicity of phase zero locations and consequently a multiplicity of phase values when each pulse reaches a reentrant center. The superposition of the phases initiated at different locations which result in a further multiplicity of phases at each reentry location such that the sum of these wave fronts extinguishes multiple reentry circuits simultaneously or within a given pulse cycle at a multiplicity of locations and, in one embodiment, at all reentry locations.

Accordingly, the present invention falls into the classification of far-field pacing therapies, since the true therapeutic effect is only achieved when a multiplicity of distant field sources initiate activation wave fronts that superpose in the manner analogous to the onset of fibrillation to cancel the multi-cyclic interference induced by the heterogeneity of the diseased cardiac tissue. The effect is analogous to noise-cancelling headphones. The primary difference being the cardiac case and the sound wave case is that the noise to be cancelled is not time invariant, and thus cannot be statically cancelled based on bandwidth consideration. In the present instance, the frequencies to be cancelled are constantly evolving, and their evolution can only be described from a bandwidth perspective in terms of their combined limit cycle structure. Thus, corrective technique must be based in an abstract space rather than the actual state space of the cardiac tissue. The space utilized in the present invention is called a Poincare space, but other spaces where the dynamics within the space takes a point and maps it back onto itself are also amenable to the methods described herein.

In accordance with the present invention, a procedure for stabilization of living tissue contractions involves monitoring the timing of intervals between contractile beats and experimental determination of interbeat intervals measured at a multiplicity of locations in response to a single stimulus intervention pulse. This single stimulus source can be initiated at any one of the multiple electrodes positioned on the tissue. Furthermore, the response or wave propagation can also be measured at each electrode. Thus a multiplicity of parameter spaces can be constructed and examined for limit cycle behavior.

For example, the usual and primary map is one that relates a prior beat interval to a subsequent beat interval. But in addition to this primary map, which is useful in identifying stable limit cycles, other maps can be constructed. For example, such a map can be created for each of the electrodes, and each will be slightly different depending on the proximity of a given electrode to a stable region. Thus these maps in totality provide a 2-dimension representation of the limit cycle, and not a one-dimensional representation that is the consequence of a single point generated map. Furthermore, correlations or time intervals between electrodes can be studied. And also importantly, the magnitudes of these signals at the various electrode positions can be used to weight this data or provide distance measures regarding rotor centers.

Generically, this type of data collection will be called inter-beat monitoring and can be used to measure intervals, magnitudes, time delays, and correlations between electrodes. Clinically, this type of data collection is to be performed during a learning phase typically lasting approximately 5 to 60 seconds in order to determine by real time calculation the approximate locations of the unstable fixed point of a chaotic regime at the intersection of its stable and unstable directions (manifolds) plotted as a function of the observable inter-beat interval change.

After a map of the limit cycle structure of the cardiac tissue is obtained, a secondary learning Poincare comprises the introduction of stimulus pulses to observe the tissue response within the calculated limit cycle structure. This data provides vectorial information about the direction in which beat intervals drift when located adjacent to limit cycles. With this information, one can place established limit cycles in a region of gradient which will consistently cause one limit cycle to evolve into another. This information is useful in not only establishing a more regular beat frequency but also useful in walking a stabilized beat frequency toward lower frequency limit cycles. This is important, since merely stabilizing a cardiac rhythm is not sufficient if the stabilizing rhythm is abnormally high and results in a condition of oxygen debt.

After a stabilization pulse is emitted, an intervention waiting period is instituted based on the close approach of the inter-beat interval timing to the unstable fixed point, such intervention being based on switching of the chaotic regime to a periodic condition according to natural system behavior. Thus at the end of such waiting period, intervention by premature injection of a stimulus pulse causes a shift to an interbeat interval system state point as a variable, lying on the stable manifold path from which it monotonically approaches the unstable fixed point, by exclusive increase or decrease of such variable. An important aspect of the present approach therefore involves real time measurement and exploitation of the aforesaid natural behavior without any theoretical model.

The aforementioned intervention waiting period is terminated by said premature injection of the stimulus pulse causing advance of the inter-beat interval and movement of the system state point onto the stable manifold toward the unstable fixed point. If the next spontaneous pulse beat corresponds to an inter-beat interval point close to the unstable fixed point, the intervention phase is terminated and the behavior stabilization program is reinitiated. Otherwise, another intervention stimulus pulse is injected.

The foregoing behavior stabilization program of monitoring inter-beat intervals, performing real time calculations and delaying premature injection of stimulus pulses, if applied by way of example to the control system of a cardiac pacemaker should restore or resume periodic cardiac beat control activity. Thus, the present disclosure can be used in conjunction with a conventional pacemaker.

The present behavior stabilization program is based on the recognition that the chaotic regime of cardiac tissue is characterized by natural motion of inter-beat interval points along unstable paths toward or away from the unstable fixed point and such chaos is controllable by a properly delayed intervention of injected stimulus pulses tending to shorten the inter-beat interval.

The methods and devices of the present disclosure, in some embodiments, exploit virtual electrode polarization to extinguish reentrant circuits. Virtual electrode polarization can be established in heterogeneous regions of cardiac tissue, and these regions coincidentally also correspond to regions comprising the core of reentry circuits. Heterogenous regions will be more polarized in response to an applied electric field than a more homogeneous region. Thus, regions near cores of reentry can be preferentially excited with very small electric fields to destabilize or terminate anchored reentrant circuits.

In conditions of extreme contractile irregularity generally more than one reentrant core is in effect, and their mutual interactions serve to reinforce the overall chaotic behavior. Thus destabilizing even one of the reentrant circuits can significantly enhance contractile regularity. Once the reentrant cores are partially destabilized, subsequent pulses can more easily terminate the arrhythmia and restore normal sinus rhythm. Accordingly, it is important to regularly reassess the limit cycle structure of the Poincare map as the therapy is applied.

A particular advantage of at least some embodiments is the use of multiple electrodes for sensing and applying stimulus pulses. Consequently, virtual electrode polarization can be achieved from a multiplicity of source positions. Generally, far-field excitation of multiple areas of atrial tissue at once can be achieved by a single source. However, when multiple sources are available the efficacy of a virtual electrode polarization can be enhanced by preferred location.

The methods of the present disclosure are useful in regularizing a chaotic state of contractility in cardiac tissue, for example tachycardia or fibrillation. In both tachycardia and fibrillation, the present strategy comprises first regularizing the contractility at generally a high frequency and then, through a series of perturbations, walks the system through a series of lower frequency limit cycles. Consequently, this program differs from conventional defibrillation therapy, which typically uses only one high-energy (about one to about seven joules) monophasic or biphasic shocks or two sequential monophasic shocks from two different vectors of far-field electrical stimuli. Accordingly, it is another advantage of the present disclosure to provide a regularization therapy which is not painful to the patient. The therapy is painless since the perturbing pulses are low energy, and the desired final state is achieved through a series of small, perturbing steps.

To further optimize this low energy method of cardiac arrhythmia termination, multiple electric field configurations can be used to optimally excite the excitable gap near the core of reentry and disrupt the reentrant circuit. More generally, the methods of the present disclosure are intended to achieve disruptions at a multiplicity of reentry circuits by avoiding a discrete approach typical of methodologies that seek superposition annihilation of a single inhomogeneity source. By sensing and developing a strategy based on the limit cycle structure as deduced from a multiplicity of sensing electrodes the combined effect of multiple reentry circuits is captured, as well as coincident episodes of stability.

These sensing and stimulative configurations can be achieved by placing several defibrillation leads/electrodes into the coronary sinus (with the possibility of both distal and proximal electrodes), the right atrial appendage, and the superior venae cavae.

In another embodiment, an electrode can be placed in the atrial septum. Electric fields can be delivered between any two or more of these electrodes as well as between one of these electrodes and an implanted control device.

In another aspect, segmented electrodes with the ability to selectively energize one or more of the electrode segments can be used. Modulation of the electric field vector can then be used to achieve maximum coverage of the entire atria within one set of shock applications or on a trial-to-trial basis.

The optimal electric fields used and the correct sequence of fields can also be explored on a trial-and-error basis for each patient.

The methods and devices of embodiments of the present disclosure can utilize a low-voltage phased unpinning far-field therapy to destabilize or terminate multiple cores of activation wave rotation, these cores are typically associated with regions of myocardial heterogeneity such as the intercaval region or fibrotic areas. A 100-fold reduction in defibrillation energy can be obtained with this unpinning method compared with conventional high-energy defibrillation, thus enabling successful cardioversion or ventricular defibrillation without exceeding the pain threshold of a patient.

As described above, virtual electrode excitation occurs both when a therapeutic pulse is delivered and also when a normal excitation wave impinges on the heterogeneity. The effect is both the cause of the contractile instability and one aspect of its remediation. Thus, it is important that the therapeutic pulse be timed properly to destabilize as many reentrant centers as possible. Most methodologies that are based on this technique are concerned with destabilizing a single reentrant center. Generally the period of a train of therapeutic pulses is selected to be less than the target core reentrant periodicity, such that at least one of the pulses arrives at the target core at the appropriate moment for initiating a counter circling reentry wave that subsequently annihilates the reentrant condition by destructive superposition. However, in the present methodology, the limit cycle structure of the contractile tissue globally is first assessed, and the timing of a therapeutic pulse is selected to force the cardiac tissue in a more regularized state rather than selecting a pulse frequency intended to annihilate a single reentrant circuit. Such a strategy may not annihilate any one reentrant circuit, but may have the effect of destabilizing all of them to various degrees such that the global system behavior is more stable.

Various shock protocols for a limit cycle phased unpinning far-field therapy to terminate atrial arrhythmias in accordance with aspects of the present disclosure are contemplated. In one aspect, multiple reentry circuits are either terminated directly or destabilized and then terminated by additional stimuli. The low energy stimulation can be below the pain threshold and, thus, may cause no anxiety and uncomfortable side effects to the patient.

In another aspect, a limit cycle phased unpinning far-field therapy can be delivered in response to a detected ventricular arrhythmia. The difference between the two therapies is largely the choice of electrode positions. Additionally, post treatment pacing may be administered as a follow-up therapy to the phased unpinning far-field therapy.

Both ventricular and atrial arrhythmias are maintained by a reentry mechanism. Specifically, cardiac tissue continually excites itself, creating reentrant, e.g. circular or tornado-like patterns of excitation. One type of self-excitation can be characterized as a macro-reentrant circuit, which can rotate around a functional or anatomic line of block. Major anatomical structures are usually involved in defining one or several simultaneous reentry circuit(s), including the region between superior and inferior venae cavae in the right atrium, and the pulmonary vein region in the left atrium. Another type of self-excitation is characterized by long cycle lengths in which one-to-one conduction occurs throughout the entire cardiac tissue. However, if the cycle lengths of reentry circuits are sufficiently short, or the result of multiple reentrant circuits generates fractionation of the waves, then the waves of excitation produced by the reentrant circuits break up in the surrounding cardiac tissue and a condition of fibrillation can ensue.

Tachycardia is defined as the presence of a single, constant, and stable reentrant circuit. Fibrillation, on the other hand, can be due to random activation in which multiple reentrant wavelets of the leading circle type wave continuously circulate in directions determined by local excitability, refractoriness, and anatomical structure. The present strategy is to first stabilize a fibrillation condition to a tachycardia condition which then can be converted to a slower rate of contractility. Accordingly, the present disclosure is applicable to both conditions.

High frequency far-field electric stimulation has been shown to result in significantly higher defibrillation success compared to near-field ATP. Our approach vastly increases the efficacy of the far-field approach by targeting the global limit cycle structure of the cardiac tissue rather than any one reentrant condition.

Embodiments of methods and apparatus in accordance with the present disclosure provide for a staged treatment for arrhythmia within pain tolerance thresholds of a patient. An arrhythmia treatment in accordance with various embodiments includes an implantable therapy generator adapted to generate and selectively deliver a staged therapy and at least two leads operably connected to the implantable therapy generator, each lead having at least one electrode adapted to be positioned proximate the atrium or ventricle of a heart of a patient. The atrial arrhythmia treatment device is programmed with a set of data collection routines which when completed output therapy parameters for delivering a staged therapy to a patient via a far-field configuration intended to treat the arrhythmic condition globally. Optionally, the method may include a near-field configuration of electrodes which upon detection of an arrhythmia, are employed by the arrhythmia treatment device.

The staged arrhythmia therapy includes a first stage for assessing the global limit cycle structure of the target cardiac tissue. Limit cycle spectra are obtained, wherein the limit cycles themselves may be represented in a number of parameter spaces. For example, a two dimensional representation may be constructed such that one axis represents a beat period at a time T and the second axis represents a beat period at a later time T+1, and these two periods are depicted as a single point in the representation P(T, T+1), such that the next period pair P(T+1, T+2) is plotted as a second point where P(T, T+1)→P(T+1, T+2).

Other representations are also valid, and may be chosen based on their therapeutic value. In particular, part of the assessment stage may include cycling through a variety of limit cycle representations where the one with a clinically valued global structure is selected. For example, the criterion for selection of a limit cycle representation may include the representation with the highest number of stable limit cycles, the representation with the lowest frequency limit cycle, or any number of clinically relevant endpoints.

Other limit cycle representations include producing a representation as described above for each of the electrode positions and choosing among these, and combining these chosen representations to produce correlation or difference representations, choosing a different pair set, such as P(T, T+n), where n can be any number. The different ways for representing limit cycle structure in a chaotic system are well known in the art, and any of these may apply to the present disclosure.

The methodologies described herein are limit cycle based, and are not based on individual pinned activation wave rotors. However, the effect of this limit cycle based approach is to act on at least one pinned rotor. The first effect of the present approach is to begin the unpinning of one or more rotation centers associated with an arrhythmia. A second effect is the reinforcement of the resulting stable limit cycle structure which has the consequence of preventing re-pinning of the one or more rotation centers associated with the arrhythmia. A third effect is to restore the pumping efficiency of the associated cardiac tissue, and simultaneously provide enhanced blood flow to the cardiac tissue as well as a reduction of the amount of oxygen required to produce a unit volume of blood flow. This last effect is important in instances where chronic support is unwanted or unneeded. In many cases the associated cardiac tissue is capable of sustaining regular contractility and requires only restoration to a more normal pumping efficiency in order to reduce hypersensitivity to reentrant circuits.

In other embodiments specific to atrial fibrillation, a cardioversion routine may be employed. In this case, a first stage has at least two and less than ten biphasic atrial cardioversion pulses. The intensity of these pulses is typically more than 10 volts and less than 100 volts with a pulse duration of less than 10 milliseconds. The pulse coupling interval is typically in the range of between 20 to 50 milliseconds. The first stage has a total duration of less than two cycle lengths of the arrhythmia and is triggered in relation to an R-wave and delivered within a ventricular refractory period. The energy of each biphasic atrial cardioversion pulse is to be less than 0.1 joules. A similar approach can be applied to ventricular fibrillation.

In yet other embodiments, far-field pulses can be intermixed with near field pulses. The far-field pulses will typically be less than the ventricular far field excitation threshold of approximately 10 volts with individual pulse duration of more than 5 and less than 20 milliseconds. In many cases, there is a benefit in coupling consecutive pulses, these pulses being applied according to timing information derived from the limit cycle structure, applying consecutive pulses in an interval of between 70-90% of the cycle length of the arrhythmia. In the case of near field pulses, these pulses have an amplitude of less than 10 volts with a pulse duration of more than 0.2 and less than 5 milliseconds and a pulse coupling interval of between 70-90% of the cycle length of the arrhythmia.

In yet another embodiment, certain arrhythmias are not responsive to cardioversion or defibrillation therapy. In this case, stabilizing the arrhythmia and partially decreasing the oxygen debt of the cardiac tissue can significantly improve cardiac tissue responsiveness to cardioversion or defibrillation pulses.

The prior three embodiments may comprise a serial therapy, wherein each approach is applied in succession. In this case, the application of each therapy approach may be delayed with an inter-stage delay of between 100 to 400 milliseconds.

In various embodiments, an atrial/ventricular arrhythmia treatment apparatus includes at least one electrode adapted to be implanted proximate an atrium/ventricle of a heart of a patient to deliver far field pulses and at least one electrode adapted to implanted proximate the atrium/ventricle of the heart of the patient to deliver near field pulses and sense cardiac signals.

An implantable therapy generator is operably connected to the electrodes and includes a battery system operably coupled and providing power to sensing circuitry, detection circuitry, control circuitry and therapy circuitry of the implantable therapy generator. The sensing circuitry senses cardiac signals representative of atrial activity and ventricular activity. The detection circuitry evaluates the cardiac signals representative of atrial/ventricular activity to determine an atrial/ventricular cycle length and detect an atrial/ventricular arrhythmia based at least in part on the atrial/ventricular cycle length.

The control circuitry, in response to the atrial/ventricular arrhythmia, controls generation and selective delivery of therapeutic pulses.

The therapy circuitry is operably connected to the electrodes and the control circuitry and includes at least one charge storage circuit selectively coupled to the at least one far field electrode that selectively stores energy. At least one second charge storage circuit selectively coupled to the at least one near field electrode that selectively stores energy.

The methods and devices of embodiments of the present disclosure can utilize a low-voltage limit cycle phased unpinning far-field therapy together with near-field to destabilize or terminate the global rotor interference structure. A significant reduction in the energy required to convert an arrhythmia can be obtained with this limit cycle based unpinning, anti-repinning and extinguishing technique compared with conventional high-energy defibrillation, thus enabling successful cardioversion/defibrillation without exceeding the pain threshold of a patient.

Applying far-field low energy electric field stimulation in a range of time- and frequency-domains consistent with the limit cycle structure of activation waves can interrupt and terminate reentrant circuits by selectively exciting the excitable gap near cores of reentry. Prior art approaches involve stimulating the excitable gap near the core of a single circuit, and thus disrupted and terminated the reentry. However, it often the product of multiple reentry waves that results in the disaggregation of wave fronts responsible for evolution in to fibrillation. Thus the target of the present approach is to disrupt the disaggregation mechanism, either by interfering with interference dynamics or by shifting the phase of individual reentrant circuits to disrupt the interference dynamics. Since reentrant circuits are often anchored at a functionally or anatomically heterogeneous region, which constitutes the core of reentry, it may be sufficient to perturb other reentrant cycles in such a way as to annihilate an adjacent reentrant cycle.

One mechanism for adjusting interference structure is to recognize that areas near the heterogeneous regions (including the region of the core of reentry) will experience greater polarization in response to an applied electric field compared with the surrounding, more homogeneous tissue. Thus, the region near the core of reentry can be preferentially excited with very small electric fields to destabilize or terminate anchored reentrant circuits. Once destabilized, subsequent shocks can more easily terminate the arrhythmia and restore normal sinus rhythm. The advantage of the present approach is that detailed knowledge about the spatial and temporal evolution of individual reentry circuits is not necessary, since the limit cycle structure represents the superposition of the individual effects. Thus, when a therapy is applied to act on the global limit cycle structure, and the effect of those therapeutic pulses on the limit cycle structure are recorded and analyzed to instruct future therapeutic pulses, which by a series of gradual adjustments shut down aspects of the global interference effects. Thus the present method enables the amelioration of all reentrant circuits simultaneously without knowing their individual spatial and temporal dynamics.

To further optimize this low energy method of termination, multiple electric field configurations corresponding to multiple electrode configurations can be used to optimally excite multiple gaps and disrupt unstable limit cycles and reinforce stable limit cycles. These field configurations can be achieved by placing several defibrillation leads/electrodes into the coronary sinus (with both distal and proximal electrodes), the right atrial appendage, and the superior venae cavae.

In another embodiment, an electrode can be placed in the atrial septum. Electric fields can be delivered between any two or more of these electrodes as well as between one of these electrodes and the device itself. In another aspect, segmented electrodes with the ability to selectively energize one or more of the electrode segments can be used. Modulation of the electric field vector can then be used to achieve maximum coverage of the entire tissue surface within one set of shock applications or on a trial-to-trial basis. The optimal electric fields used and the correct sequence of fields can also be explored on a trial-and-error basis for each patient.

In some instances a proportional perturbation feedback procedure is more effective in terminating arrhythmias. Such an algorithm begins by determining the location of a clinically useful limit cycle unstable fixed point, as well as its local stable and unstable manifolds. In some cases there may be multiple limit cycle fixed points, and in this case it is important to determine the boundary surfaces, e.g., the points in Poincare space where the attraction or repulsion between two or more fixed points is equalized. We call this structure the Poincare map.

A Poincare map can be obtained in the non-perturbed system wherein sensing electrodes collect the system state data. A Poincare map can be obtained from each of a multiplicity of sensing electrodes. If the stable, unstable and fixed points coincide in these representations, than a single sensing point can be used. However, due to localized interference, this coincidence may not be the case. Thus we can transform each Poincare map into the others by a collection of rotations and displacements, where P1P2(r,d) is the transformation of Poincare map P1 into Poincare map P2 through a rotation r and a displacement d.

Additional information about the dynamics of the system state can be obtained by employing the virtual electrode potential (VEP) approach. This methodology creates virtual voltage sources at the centers of reentrant loops, and thus contains information about the temporal relationships between activation waves emanating from these points. The intensity of the virtual electrode effect is dependent upon the distance from the far-field electrode, thus by employing far-field sources at a number of different locations, we can map out the temporal locations of these reentrant centers. By using the sensing electrodes we can then construct far-field Poincare maps. Ideally, the sensing electrode and the far-field electrodes are the same. In this case, the far-field Poincare maps can be transformed using the rotation and displacement information obtained above. The resulting transformed Poincare maps will each contain a stable and unstable manifold, these manifolds being primarily the result of individual reentrant centers. Thus one can obtain the limit cycle structure approximately for each reentrant center. Once one makes this transformation and obtain the various stable and unstable manifolds, we can now construct a composite Poincare map template comprised of these manifolds in superposition.

Now when unperturbed dynamics is mapped onto the Poincare map template we see that a current point in Poincare space is near a particular stable manifold corresponding to a particular far-field electrode. Thus the corrective pulse is to be applied to that electrode, since due to its proximity it will have a stronger effect in regularizing the beat rate. In the application of this approach, it is understood that corrective pulses will be applied at different far-field electrodes as a function of time, and consequently the system will be perturbed to follow different stable manifolds. However, all the stable manifolds will group in a subspace of the Poincare space and thus form a hyper-stable manifold. It is therefore stabilizing regardless of which particular stable manifold is targeted at a particular point in time. Furthermore, as the cardiac system is stabilized in this way the area of the hyper-stable manifold decreases. To take advantage of this effect, intermittently the far-field stimulation can be applied to recalculate the composite Poincare template. Alternatively, the position of the individual stable manifolds can be updated by observing the probabilistic structure of the beat rate resulting from perturbation therapy.

The present disclosure may be an implantable device which uses software to control arrhythmia in the atria and ventricles. Generally, the software comprises a learning routine and a control routine. Entry of measurement input data from three probes through converter to an implanted device initiates the learning routine for real time calculation of the Poincare maps. The learning routine detects and calculates inter-beat interval data from the converter is continuously monitored in the implanted device pursuant to the software until chaotic beating occurs. The interval data is then plotted to initiate the learning routine. The intervals between chaotic beats are plotted as a Poincare map wherein one axis is the current inter-beat interval I(n) and the other axis is the prior inter-beat interval I(n−1) which defines a point P(T) and time T in the Poincare map with coordinates (I(n−1), I(n)). After a series of points are plotted one or more unstable fixed points emerge. These fixed points are determined by constructing vectors from a point P(T) at T to a point P(T+1) at later time T+1.

What emerges is a series of vectors converging on a stable manifold, following the stable manifold, and terminating at the fixed point, where the vectors then diverge from the fixed point and travel along the unstable manifold. In this way, the entire Poincare map is filled with vectors indicating the flow of Poincare points in a given region, thus providing predictive power.

This predictive power can be used to construct a corrective therapy. For any given point in time, a Poincare point with respect to the stable manifold and fixed point can be examined. A decision to perturb the cardiac system and issue a therapeutic pulse may be gated by a maximum distance D from the stable manifold or fixed point. Furthermore, the local vector structure is examined to determine that the current Poincare point is in a region of vectors pointed to the stable manifold or fixed point. The intervals corresponding to the Poincare point is then examined during the next step to re-verify that the beats are not periodic. If any of the tests performed during the program steps fails, the learning routine is reinitialized. When all such tests are passed, the fixed point is recalculated.

In testing whether the dynamics is chaotic or stable, one constructs the Jacobian from the local vector field in the Poincare map. To construct the Jacobian, we call one axis of the Poincare map x and the other axis y, then we construct the time derivatives of x and y. From these equations one constructs the Jacobian matrix, and the eigenvalues are calculated. Negative real parts of the eigenvalues indicate a stable (attractive) fixed point and positive values indicate unstable (repulsive) fixed point.

The sign of the real parts of the eigenvalues is then tested to determine their signs. Consideration may also be given to the magnitude of the eigenvalues, especially when the two eigenvalues are of different sign. If the sign is not positive, beating is not chaotic and the learning phase is reinitialized. The final step of the learning routine involves system perturbation to observe the resulting change in fixed point location.

The control routine is initiated upon termination of the learning phase by determining approach to the fixed point on the Poincare map. If the approach is close (within distance D), the next calculation is triggered, whereby a stimulus pulse is inserted at the proper time and monitoring of inter-beat intervals is continued while waiting for another close approach to the fixed point.

The aperiodic behavior or arrhythmia present in the cardiac tissue involves transient high order periodicities, wherein the nth inter-beat interval I(n) has been plotted against the previous interval I(n–1) at various stages. A typical sequence of inter-beat intervals during aperiodic beating is depicted wherein a shift in the state of the system occurs toward an unstable fixed point lying on the line of identity. Thus a point lies close to stable manifold. Other points diverge from the unstable fixed point and hence reveal an unstable manifold. The local flow geometry around fixed point is that of a saddle. In this case the saddle is a flip saddle in that the distances between successive Poincare points from the fixed point monotonically increase in an exponential fashion along the unstable manifold and the Poincare points can alternate on opposite sides of the stable manifold. The flip saddle is characterized by a short inter-beat interval followed by a long interval.

In accordance with the present disclosure, perturbation of the system being monitored is effected when the Poincare point monotonically approaches the unstable fixed point, such perturbation forcing the system Poincare point onto the stable manifold. As a result, the system state point will naturally move toward the unstable fixed point rather than away from it.

The above convergence is dramatically enhanced by considering the far-field generated stable and unstable manifolds. This provides a system-wide map with alternative stable manifolds to be selected among, as described above, wherein the distance to a stable manifold is minimized. Movement of the Poincare state point toward the stable manifold by proportional perturbation feedback acting on multiple far-field generated Poincare maps is effected pursuant to the present disclosure without parameter change. Such proportional perturbation feedback method is particularly useful where the cardiac tissue preparation possesses no systemwide parameter that can be changed with sufficient rapidity to implement corrective control.

The proportional perturbation feedback procedure of the present disclosure begins by determining the location of the unstable fixed point, and the associated stable and unstable manifolds. If P(T) is the location of the current Poincare point on the Poincare map, and t is the predicted timing of the next natural beat, the required advance in timing on the perturbation pulse is dt, which is proportional to the projection of the distance from the current point P(T) to the point P(S) on the stable manifold corresponding to P(T) as determined by the local vector field. The timing of the cardiac perturbation pulse is generated by dt which represents the amount of time to shorten an anticipated natural beat to force the next Poincare point onto the stable manifold. The foregoing proportional feedback control procedure is performed during the aforementioned learning and intervention phases.

The learning routine typically requires from 5 to 60 seconds to generate the Poincare maps, after which the chaos controlling portion of the software waits for the system to make a close approach to the unstable fixed point at a Poincare point within radius D. The next point would normally fall further out along the unstable manifold (as well as on the opposite side of the stable manifold). However, at this point the implanted device intervenes pursuant to its software by injecting the electrical-stimulus early enough so that the next Poincare point actually occurs near the stable manifold. Since the system is now close to the stable manifold, ideally the subsequent spontaneous beat would tend to move closer to the fixed point along the stable manifold. Thus, Poincare points will tend to be confined to a region near the unstable fixed point, thereby regularizing the arrhythmia.

When only the unperturbed Poincare map is used, the next Poincare point typically does not fall precisely on the stable manifold. It may also not fall within the radius D to the fixed point but still falls fairly close to the stable manifold. The result is the application of corrective pulses only intermittently, which tends not to optimize cardiac output efficiency. Without improvement in output efficiency, the cardiac tissue continues to be starved of oxygen, and thus remains dependent upon the corrective pulses. In applying the far-field generated Poincare maps, the algorithm is able to better triangulate to the stable manifold, and remains responsive to induced changes in Poincare position as the point travels through different regions of cardiac tissue corresponding to each of the reentrant centers. This tighter adjustment to the stable manifold affords a markedly better output efficiency, as well as the potential for training the cardiac tissue to adjust the phases of the separate reentrant centers to an optimal or coordinate contraction.

It is interesting to note that in several cases chaos control in accordance with the present disclosure had the additional effect of eliminating the shortest inter-beat intervals, hence reducing the average rate of tachycardia. Without an understanding of the chaotic nature of the system, it would seem paradoxical that an intervention that could only shorten the inter-beat intervals would result in a lengthening of the average interval. The only plausible explanation is that by considering the topology of individual reentrant centers, and constructing Poincare maps of each, that the system tends to optimize certain periodicities while inhibiting others. By reducing the number of interacting oscillators, whatever superposition of the reduced number of activation waves will naturally have a narrower bandwidth and lower frequency. For example, it is well known that very long inter-beat intervals tend to be followed by very short inter-beat intervals (a consequence of the properties of the flip saddle), elimination of the very long intervals also tends to eliminate very short intervals. In cases in which very short intervals predominate during the arrhythmia, their elimination during chaos control will tend to lengthen the average inter-beat interval between spontaneous beats. Thus, where chaos was successfully controlled, the-chaotic pattern of the arrhythmia was converted to a low order periodic pattern.

In accordance with the present disclosure, a control method for maintenance of cardiac chaos in a system exhibiting periodicity, involves location specific application of time-dependent perturbations of parameters based on a local vector space, and location of fixed point and stable manifold information. Cardiac tissue is readily accessible to measurement and calculation as graphical points in Poincare space on a return map providing a dynamic representation of the system being monitored. The concentration of graphical measurement points within a plurality of regions are located and identified on the return map as following paths or routes toward a loss region from which periodicity follows. Transition to periodicity occurs when progression from chaos behavior along one multiple routes is initiated.

In traditional high-voltage defibrillation therapy, a truncated exponential biphasic waveform has a lower defibrillation energy as compared to monophasic shocks. However, in the case of phased unpinning far-field therapy, the use of multiple monophasic versus multiple biphasic waveforms was recently found to be more effective in terminating ventricular arrhythmias in a rabbit model. This difference is because optimal biphasic defibrillation waveforms do not produce VEPs because of an asymmetric effect of phase reversal on membrane polarization.

In the present disclosure, multiple electric field configurations are used to optimally excite the excitable gap near one or more cores of reentry and disrupt the associated reentrant circuits. These field configurations can be achieved by placing several defibrillation leads/electrodes into the coronary sinus (with both distal and proximal electrodes), the right atrial appendage, and the superior venae cavae.

In another embodiment, an electrode can be placed in the atrial septum. Electric fields can be delivered between any two or more of these electrodes as well as between one of these electrodes and the device itself. In another aspect, segmented electrodes with the ability to selectively energize one or more of the electrode segments can be used. Modulation of the electric field vector can then be used to achieve maximum coverage of the entire atria within one set of shock applications or on a trial to trial basis. The optimal electric fields used and the correct sequence of fields can also be explored on a trial and error basis for each patient.

The implanted device can be implanted just under the left clavicle. This location places the device in approximate alignment with the longitudinal anatomical axis of the heart (an axis through the center of the heart that intersects the apex and the inter-ventricular septum). When the electrodes are implanted in this manner, the arrangement of the device and electrodes is similar in configuration to the top of an umbrella: the device constituting the ferrule of an umbrella, and the electrodes constituting the tines of the umbrella. The electrodes of the device are energized in a sequential pattern as determined by the Poincare maps to achieve electrical fields of stimulation that is similar to "stimulating" particular regions of the cardiac tissue.

In another aspect, no ventricular lead is positioned, removing the need for a lead to cross a heart valve during lead implantation. Leads may be active or passive fixation.

In another aspect, the device can be fully automatic; automatically delivering a shock protocol when arrhythmias are detected. In another aspect, the device can have a manual shock delivery; the device prompting the patient to either have a doctor authorize the device to deliver a shock protocol, or the device can prompt the patient to self-direct the device to deliver a shock protocol in order to terminate a detected arrhythmia. In another aspect, the device can be semi-automatic; a "bed-side" monitoring station can be used to permit remote device authorization for the initiation of a shock protocol when atrial arrhythmias are detected.

In one embodiment of the present disclosure, the system includes an implantable housing to which is releasably attached a first atrial catheter and a ventricular catheter. The first atrial catheter has a first atrial electrode and a first defibrillation electrode and is positioned within the heart with the atrial electrode and the first defibrillation electrode in a supraventricular region of the heart. The ventricular catheter has a first ventricular electrode, and is positioned within the heart with the first ventricular electrode in a right ventricular chamber of the heart.

In an additional embodiment, the first atrial catheter further includes at least a second atrial electrode and a second defibrillation electrode. The first atrial catheter is positioned within the supraventricular region of the heart with the first atrial electrode, the first defibrillation electrode and the second atrial electrode positioned within a coronary sinus vein of the heart, and the second defibrillation electrode within the right atrium chamber or major vein leading to the heart. In a further embodiment, the elongate body of the first atrial catheter has a series of lateral deflections that mechanically biases the first atrial electrode into physical contact with the coronary sinus vein of the heart.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the spirit and scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

What is claimed is:

1. A method for stabilization of cardiac tissue contractions using limit cycles, the method comprising:
   selecting a desired limit cycle in Poincare space which is indicative of a desired state of a heart;
   mapping, in real time, a measured limit cycle in Poincare space based on measurements obtained from a first electrode disposed on the heart;
   applying a stimulus pulse with an energy of less than 0.1 joules to the heart from the first electrode, wherein the stimulus pulse induces an altered limit cycle that is different than the measured limit cycle;
   observing a change, in real time, in the altered limit cycle in response to the stimulus pulse and constructing a vector of the change;
   observing a difference between the altered limit cycle and the desired limit cycle;
   applying an intervention pulse from the first electrode if the difference exceeds a limit cycle threshold or waiting for a waiting period if the difference is within the limit cycle threshold, wherein the intervention pulse is configured to move the altered limit cycle toward the desired limit cycle.

2. The method as recited in claim 1, comprising a learning phase lasting from five seconds to sixty seconds, wherein the steps of applying the stimulus pulse and the step of observing the change occur during the learning phase.

3. The method as recited in claim 1, wherein the intervention pulse is from about 10 volts and has a pulse duration of between about 5 millisecond and 20 milliseconds.

4. The method as recited in claim 1, wherein the waiting period is between about 100 milliseconds and 400 milliseconds.

5. The method as recited in claim 4, wherein the method is continually repeated during treatment.

6. A method for stabilization of cardiac tissue contractions using limit cycles, the method comprising:
   selecting a desired limit cycle in Poincare space which is indicative of a desired state of a heart;
   mapping, in real time, a measured limit cycle in Poincare space based on measurements obtained from a first electrode and a second electrode both of which are disposed on the heart;
   applying a first stimulus pulse with an energy of less than 0.1 joules to the heart from the first electrode, wherein the first stimulus pulse induces a first altered limit cycle that is different than the measured limit cycle;
   observing a first change, in real time, in the first altered limit cycle in response to the first stimulus pulse and constructing a first vector of the first change;
   applying a second stimulus pulse with an energy of less than 0.1 joules to the heart from the second electrode, wherein the second stimulus pulse induces a second altered limit cycle that is different than the first altered limit cycle;
   observing a second change, in real time, in the second altered limit cycle in response to the second stimulus pulse and constructing a second vector of the second change;
   observing a difference between the second altered limit cycle and the desired limit cycle;
   applying an intervention pulse from the first electrode or the second electrode if the difference exceeds a limit cycle threshold or waiting for a waiting period if the difference is within the limit cycle threshold, wherein the intervention pulse is configured to move the second altered limit cycle toward the desired limit cycle.

7. The method as recited in claim 6, comprising a learning phase lasting from five seconds to sixty seconds, wherein the steps of applying the stimulus pulse and the step of observing the change occur during the learning phase.

8. The method as recited in claim 6, wherein the intervention pulse is from about 10 volts and has a pulse duration of between about 5 millisecond and 20 milliseconds.

9. The method as recited in claim 6, wherein the waiting period is between about 100 milliseconds and 400 milliseconds.

10. The method as recited in claim 9, wherein the method is continually repeated during treatment.

11. The method as recited in claim 6, wherein the heart is an in situ heart.

12. A program storage device readable by machine, tangibly embodying a program of instructions executable by machine to perform method steps for stabilization of cardiac tissue contractions using limit cycles, the method comprising:
  selecting a desired limit cycle in Poincare space which is indicative of a desired state of a heart;
  mapping, in real time, a measured limit cycle in Poincare space based on measurements obtained from a first electrode and a second electrode both of which are disposed on the heart;
  applying a first stimulus pulse with an energy of less than 0.1 joules to the heart from the first electrode, wherein the first stimulus pulse induces a first altered limit cycle that is different than the measured limit cycle;
  observing a first change, in real time, in the first altered limit cycle in response to the first stimulus pulse and constructing a first vector of the first change;
  applying a second stimulus pulse with an energy of less than 0.1 joules to the heart from the second electrode, wherein the second stimulus pulse induces a second altered limit cycle that is different than the first altered limit cycle;
  observing a second change, in real time, in the second altered limit cycle in response to the second stimulus pulse and constructing a second vector of the second change;
  observing a difference between the second altered limit cycle and the desired limit cycle;
  applying an intervention pulse from the first electrode or the second electrode if the difference exceeds a limit cycle threshold or waiting for a waiting period if the difference is within the limit cycle threshold, wherein the intervention pulse is configured to move the second altered limit cycle toward the desired limit cycle.

13. The program storage device as recited in claim 12, comprising a learning phase lasting from five seconds to sixty seconds, wherein the steps of applying the stimulus pulse and the step of observing the change occur during the learning phase.

14. The program storage device as recited in claim 12, wherein the intervention pulse is from about 10 volts and has a pulse duration of between about 5 millisecond and 20 milliseconds.

15. The method as recited in claim 12, wherein the waiting period is between about 100 milliseconds and 400 milliseconds.

16. The program storage device as recited in claim 15, wherein the method is continually repeated during treatment.

17. The program storage device as recited in claim 12, wherein the heart is an in situ heart.

* * * * *